United States Patent
Park et al.

(10) Patent No.: US 9,921,487 B2
(45) Date of Patent: Mar. 20, 2018

(54) METHOD FOR INSPECTING PHOTORESIST PATTERN

(71) Applicant: Samsung Electronics Co., Ltd., Suwon-si, Gyeonggi-do (KR)

(72) Inventors: Kyung Jae Park, Suwon-si (KR); Wooseok Shim, Osan-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/252,952

(22) Filed: Aug. 31, 2016

(65) Prior Publication Data
US 2017/0103924 A1    Apr. 13, 2017

(30) Foreign Application Priority Data
Oct. 8, 2015    (KR) .................. 10-2015-0141759

(51) Int. Cl.
| | | |
|---|---|---|
| G03F 7/20 | (2006.01) | |
| G01N 21/00 | (2006.01) | |
| G03F 7/09 | (2006.01) | |
| G03F 7/105 | (2006.01) | |
| G03F 7/40 | (2006.01) | |

(52) U.S. Cl.
CPC ......... *G03F 7/70625* (2013.01); *G01N 21/00* (2013.01); *G03F 7/091* (2013.01); *G03F 7/105* (2013.01); *G03F 7/40* (2013.01); *G03F 7/405* (2013.01); *G03F 7/70608* (2013.01)

(58) Field of Classification Search
None
See application file for complete search history.

(56) References Cited

U.S. PATENT DOCUMENTS

| | | | |
|---|---|---|---|
| 4,268,603 A | | 5/1981 | Sato |
| 4,668,335 A | * | 5/1987 | Mockler ........... H01L 21/02071 257/E21.309 |
| 5,798,525 A | | 8/1998 | Benizri-Carl et al. |
| 6,091,488 A | * | 7/2000 | Bishop ................. G01N 21/956 356/237.5 |
| 6,103,456 A | * | 8/2000 | Tobben ............... H01L 21/0276 257/E21.029 |

(Continued)

FOREIGN PATENT DOCUMENTS

| | | |
|---|---|---|
| KR | 10-2009-0069093 A | 6/2009 |
| KR | 10-1095062 B1 | 12/2011 |

OTHER PUBLICATIONS

Stefan W. Hell et al., Breaking the diffraction resolution limit by stimulated emission: stimulated-emission-depletion fluorescence microscopy; Optics Letters, vol. 19, No. 11, Jun. 1, 1994.

*Primary Examiner* — Kimberly Rizkallah
*Assistant Examiner* — Bo Bin Jang
(74) *Attorney, Agent, or Firm* — Harness, Dickey & Pierce, P.L.C.

(57) ABSTRACT

Example embodiments of inventive concepts provide a method for inspecting and/or observing photoresist patterns. The inspecting and/or observing methods may include forming at least an anti-reflective layer on a substrate, forming a fluorescent photoresist pattern on the anti-reflective layer, the fluorescent photoresist pattern having fluorescence, and observing and/or inspecting a shape of the fluorescent photoresist pattern using a fluorescence microscope.

4 Claims, 13 Drawing Sheets

(56) References Cited

U.S. PATENT DOCUMENTS

| | | | |
|---|---|---|---|
| 7,085,676 B2 | 8/2006 | Opsal et al. | |
| 7,179,568 B2 | 2/2007 | Cerrina et al. | |
| 7,304,302 B1 | 12/2007 | Nunan et al. | |
| 7,527,920 B2 | 5/2009 | Goldstein et al. | |
| 7,626,694 B2 | 12/2009 | Betzig et al. | |
| 7,751,046 B2 | 7/2010 | Levy et al. | |
| 8,765,496 B2 | 7/2014 | Nasser-Ghodsi et al. | |
| 2001/0001698 A1* | 5/2001 | Grober | G03F 7/0045 430/139 |
| 2002/0001768 A1* | 1/2002 | Feke | G03F 7/0045 430/139 |
| 2004/0196455 A1* | 10/2004 | Ermantraut | G01N 21/6452 356/243.1 |
| 2006/0286811 A1* | 12/2006 | Heiden | G01N 21/6456 438/759 |
| 2013/0068967 A1* | 3/2013 | Kleppe | G01N 21/6458 250/459.1 |
| 2014/0193841 A1 | 7/2014 | Welch et al. | |

* cited by examiner

METHOD FOR INSPECTING PHOTORESIST PATTERN

CROSS-REFERENCE TO RELATED APPLICATION

This U.S. non-provisional patent application claims priority under 35 U.S.C. § 119 to Korean Patent Application No. 10-2015-0141759, filed on Oct. 8, 2015, in the Korean Intellectual Property Office (KIPO), the disclosure of which is hereby incorporated by reference in its entirety.

BACKGROUND

1. Field

Inventive concepts relate to a method for inspecting and/or observing a photoresist pattern using a fluorescence microscope and/or fluorescence metrology tool.

2. Description of Related Art

As design rules of semiconductor devices have been rapidly reduced, photolithography processes for forming patterns of semiconductor devices have been increasingly difficult. Wafers or semiconductor devices can be greatly deteriorated by a little deformation of a photoresist pattern. Accordingly, inspection processes are performed on photoresist patterns formed on the wafers.

SUMMARY

Example embodiments of inventive concepts may provide a method for inspecting and/or observing photoresist patterns capable of improving resolution and reliability.

In example embodiments, a method for inspecting and/or observing a photoresist pattern may include forming an anti-reflective layer on a substrate, forming a fluorescent photoresist pattern on the anti-reflective layer, the fluorescent photoresist pattern having fluorescence, and observing and/or inspecting a shape of the fluorescent photoresist pattern using a fluorescence microscope.

In example embodiments, the forming the fluorescent photoresist pattern may include forming a photoresist layer on the anti-reflective layer, the photoresist layer including at least one fluorescent additive, and performing a photolithography process on the photoresist layer.

In example embodiments, the at least one fluorescent additive may include a first fluorescent additive and a second fluorescent additive, and the first fluorescent additive and the second fluorescent additive may include fluorescent colors that are different from each other.

In example embodiments, the forming the fluorescent photoresist pattern may include forming a photoresist layer including a fluorescent resin on the anti-reflective layer, and performing a photolithography process on the photoresist layer.

In example embodiments, the forming the fluorescent photoresist pattern may include forming a photoresist layer on the anti-reflective layer, performing a photolithography process on the photoresist layer to form a preliminary photoresist pattern, and injecting a conditional fluorescent material into the preliminary photoresist pattern, the conditional fluorescent material having a property of showing fluorescence under an acid condition. A pattern of the fluorescent photoresist pattern may correspond to a pattern of the preliminary photoresist pattern.

In example embodiments, the injecting the conditional fluorescent material may include reacting the condition fluorescent material with an acid included in the preliminary photoresist pattern to show the fluorescence.

In example embodiments, the injecting the conditional fluorescent material may include injecting the conditional fluorescent material into the anti-reflective layer exposed by the preliminary photoresist pattern. The conditional fluorescent material injected in the anti-reflective layer may not show the fluorescence.

In example embodiments, the forming the fluorescent photoresist pattern may include forming a photoresist layer on the anti-reflective layer, performing a photolithography process on the photoresist layer to form a preliminary photoresist pattern, and forming a conditional fluorescent material layer around the preliminary photoresist pattern. The conditional fluorescent material layer may have a property of showing the fluorescence under an acid condition. The fluorescent photoresist pattern may correspond to a structure including the preliminary photoresist pattern and the conditional fluorescent material layer covering the preliminary photoresist pattern.

In example embodiments, the conditional fluorescent material layer may react with an acid included in the preliminary photoresist pattern to show the fluorescence.

In example embodiments, the forming the conditional fluorescent material layer may include reacting the conditional fluorescent material layer with an acid included in the preliminary photoresist pattern to show the fluorescence.

In example embodiments, the forming the conditional fluorescent material layer may include forming the conditional fluorescent material layer to extend onto the anti-reflective layer exposed by the preliminary photoresist pattern, and portions of the conditional fluorescent material layer on the anti-reflective layer exposed by the preliminary photoresist pattern may not show the fluorescence.

In example embodiments, the fluorescence microscope may be a microscope configured to use at least one of reversible saturable optical fluorescence transitions (RESOLFT) and a stochastic functional technique.

In example embodiments, a method for inspecting and/or observing a photoresist pattern may include forming a fluorescent anti-reflective layer on a substrate, the fluorescent anti-reflective layer having fluorescence; forming a photoresist pattern on the fluorescent anti-reflective layer; and observing and/or inspecting a shape of the photoresist pattern using a fluorescence microscope.

In example embodiments, the fluorescent anti-reflective layer may include at least one fluorescent additive.

In example embodiments, the photoresist pattern may be configured to block light generated from the fluorescent anti-reflective layer from passing through the photoresist pattern. The observing and/or inspecting the shape of the photoresist pattern may include observing and/or inspecting a shape of the fluorescent anti-reflective layer exposed by the photoresist pattern using the fluorescence microscope.

In example embodiments, the fluorescence microscope may be configured to use at least one of a reversible saturable optical fluorescence transitions (RESOLFT) and a stochastic functional technique.

In example embodiments, a method for inspecting a photoresist pattern may comprise forming a multi-layer structure on a substrate, the multi-layer structure including the photoresist pattern, one layer of the multi-layer structure having fluorescence; and inspecting the photoresist pattern using a fluorescence microscope.

In example embodiments, the fluorescence microscope may be configured to use at least one of a reversible saturable optical fluorescence transitions (RESOLFT) or a stochastic functional technique.

In example embodiments, the photoresist pattern may include at least one fluorescent additive, the at least one fluorescent additive includes a first fluorescent additive and a second fluorescent additive that have different colors from each other, and the one layer of the multi-layer structure having fluorescence may be the photoresist pattern.

In example embodiments, the forming the multi-layer structure may include forming an anti-reflective layer on the substrate and forming the photoresist pattern on the anti-reflective layer, and the one layer of the multi-layer structure having fluorescence may be the anti-reflective layer.

In example embodiments, the one layer of the multi-layer structure may have fluorescence in the photoresist pattern; and the forming the multi-layer structures includes, forming a photoresist layer on the substrate, performing a preliminary photolithography process on the photoresist layer to form a preliminary photoresist pattern, and injecting a conditional fluorescent material into the preliminary photoresist pattern, the conditional fluorescent material having a property showing fluorescence under an acid condition.

BRIEF DESCRIPTION OF THE DRAWINGS

The foregoing and other features of inventive concepts will become more apparent from the more particular description of non-limiting embodiments of inventive concepts, as illustrated in the accompanying drawings in which like reference characters refer to like parts throughout the different views. The drawings are not necessarily to scale, emphasis instead being placed upon illustrating principles of inventive concepts. In the drawings.

DETAILED DESCRIPTION OF EXAMPLE EMBODIMENTS

Figure 1:
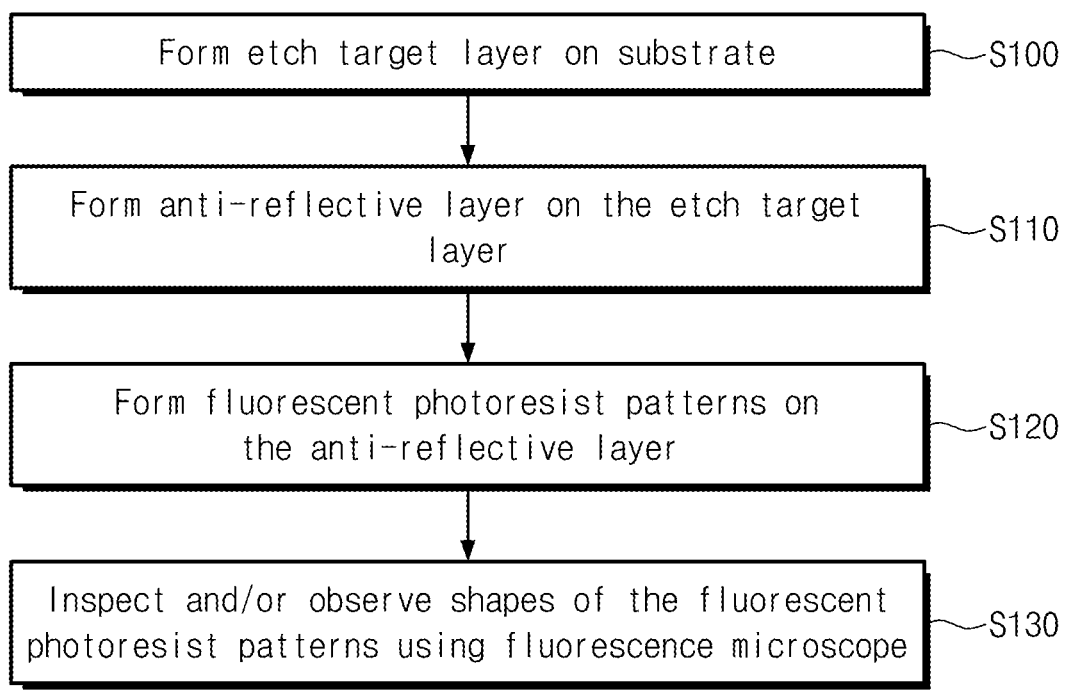
FIG. 1 is a flow chart illustrating a method for inspecting and/or observing a photoresist pattern, according to example embodiments of inventive concepts.

Inventive concepts will now be described more fully hereinafter with reference to the accompanying drawings, in which example embodiments of inventive concepts are shown. Inventive concepts and methods of achieving them will be apparent from the following example embodiments that will be described in more detail with reference to the accompanying drawings. Example embodiments of inventive concepts may, however, be embodied in many different forms and should not be constructed as being limited to the embodiments set forth herein. Rather, these example embodiments are provided so that this disclosure will be thorough and complete, and will fully convey the scope of example embodiments of inventive concept to those of ordinary skilled in the art.

The terminology used herein is for the purpose of describing particular embodiments only and is not intended to be limiting of example embodiments. As used herein, the singular terms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

It will be understood that when an element is referred to as being "connected" or "coupled" to another element, it may be directly connected or coupled to the other element or intervening elements may be present. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an etched region or an implanted region illustrated as a rectangle may have rounded or curved features. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Example embodiments of inventive concepts explained and illustrated herein include their complementary counterparts. The same reference numerals or the same reference designators denote the same elements throughout the specification. Like reference characters and/or numerals in the drawings denote like elements, and thus their description may not be repeated.

Figure 2A:
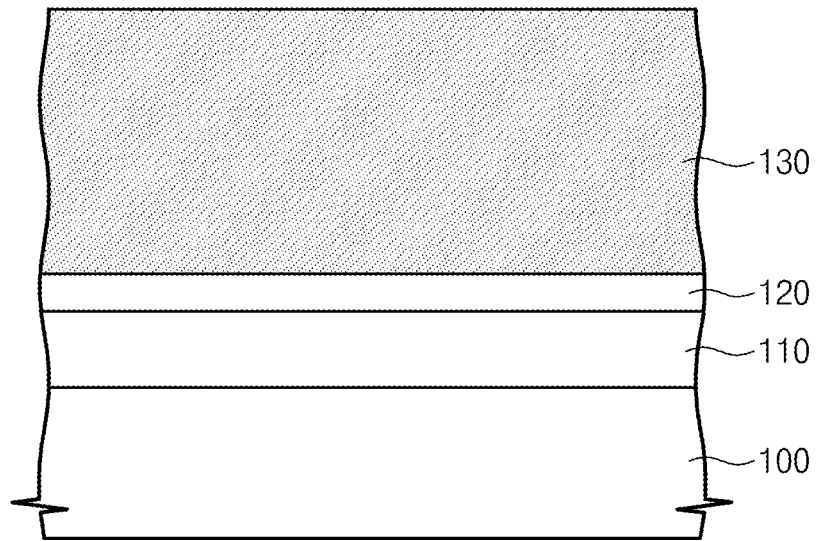
FIGS. 2A and 2B are cross-sectional views illustrating the method for inspecting and/or observing a photoresist pattern of FIG. 1.
Figure 2B:
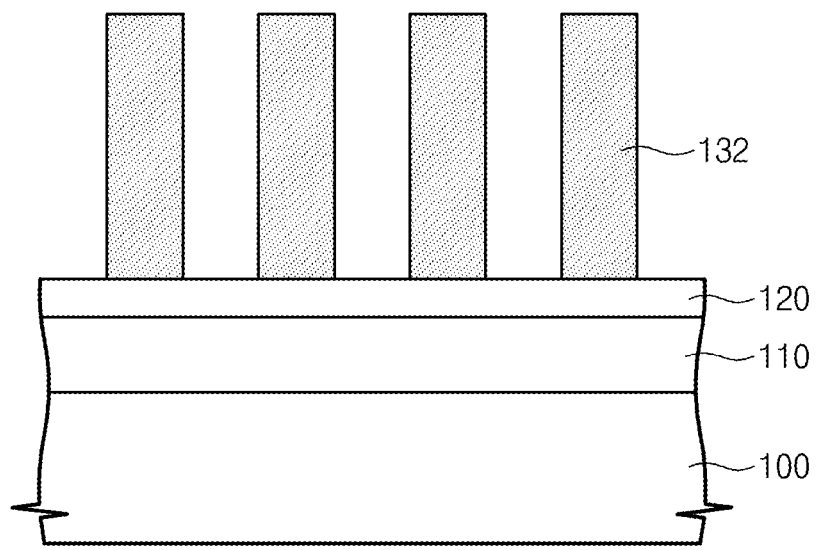
Figure 3:
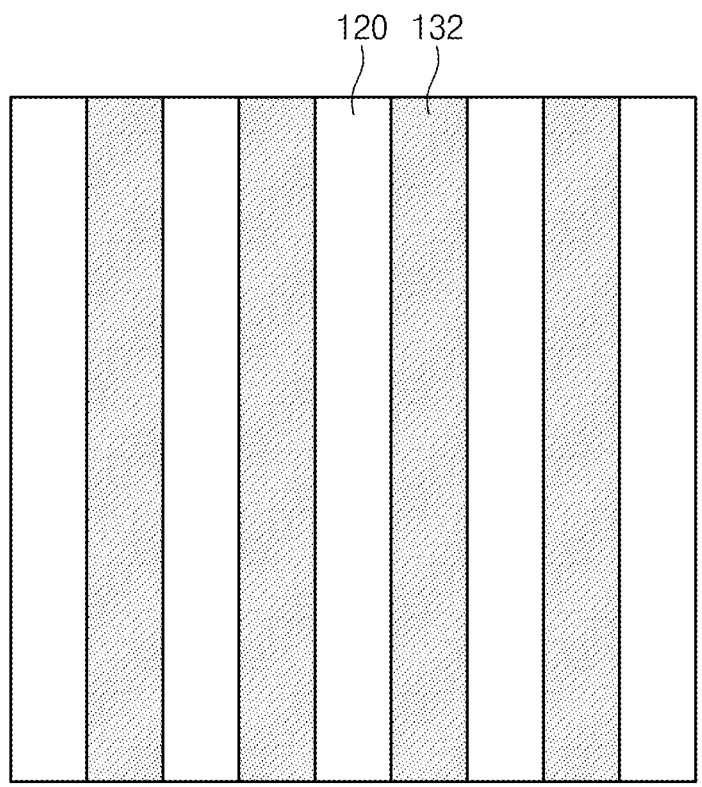
FIG. 3 schematically illustrates a planar image of a structure of FIG. 2B or 5C obtained using a fluorescence microscope.

FIG. 1 is a flow chart illustrating a method for inspecting and/or observing a photoresist pattern, according to example embodiments of inventive concepts. FIGS. 2A and 2B are cross-sectional views illustrating the method for inspecting and/or observing a photoresist pattern of FIG. 1. FIG. 3 schematically illustrates a planar image of a structure of FIG. 2B obtained using a fluorescence metrology tool (e.g., fluorescence microscope). For ease of description, examples hereinafter are described where fluorescence microscope is used to inspect and/or observe a photoresist pattern. However, inventive concepts are not limited thereto and other types of fluorescence metrology tools may be used to inspect and/or observe photoresist patterns.

Referring to FIGS. 1 and 2A, an etch target layer 110 may be formed on a substrate 100 (S100). The substrate 100 may be a semiconductor substrate, a glass substrate, or a polymer substrate, but is not limited thereto. In example embodiments, when the substrate 100 is a semiconductor substrate, the substrate 100 may include at least one of crystalline silicon, amorphous silicon, and silicon-germanium. The substrate may be doped with dopants (e.g., silicon doped with dopants).

The etch target layer 110 may include a semiconductor material, a conductive material, or an insulating material. In example embodiments where the etch target layer 110 includes the semiconductor material, the etch target layer 110 may be a portion of the semiconductor substrate 100, an epitaxial layer formed of a semiconductor material, or a semiconductor layer deposited on the substrate 100. In example embodiments where the etch target layer 110 includes the conductive material, the etch target layer 110 may include doped poly-silicon, a metal, a metal silicide, a metal nitride, or any combination thereof. In example embodiments where the etch target layer 110 includes the insulating material, the etch target layer 110 may include silicon oxide, silicon nitride, or silicon oxynitride, but is not limited thereto. The etch target layer 110 may be a single layer or a multi-layer including a plurality of stacked layers. In example embodiments, the etch target layer 110 may include a plurality of stacked insulating layers and a conductive or semiconductor layer disposed between the stacked insulating layers. The etch target layer 110 may be formed using, for example, including but not limited to, a chemical vapor deposition (CVD) method, a physical vapor deposition (PVD) method, and/or an atomic layer deposition (ALD) method.

Referring to FIGS. 1 and 2A, an anti-reflective layer 120 may be formed on the etch target layer 110. The anti-reflective layer 120 may limit (and/or prevent) uniformity of critical dimensions (CDs) of fluorescent photoresist patterns 132 of FIG. 2B to be described later from being deteriorated by reflected light. The anti-reflective layer 120 may be formed by, for example, including but not limited to, a spin coating process. In example embodiments, the anti-reflective layer 120 may include fluorescence. However, hereinafter, the anti-reflective layer 120 not having the fluorescence will be described as an example for the purpose of ease and convenience in explanation. The anti-reflective layer 120 having the fluorescence will be described later with reference to FIG. 9.

Still referring to FIGS. 1 and 2A, a photoresist layer 130 may be formed on the anti-reflective layer 120. The photoresist layer 130 may be formed by, for example, including but not limited to, a spin coating process. The photoresist layer 130 may include but not limited to, a resin, a photosensitive material, and an additive.

The photoresist layer 130 may have fluorescence. According to example embodiments, the photoresist layer 130 may include at least one of a fluorescent additive or a fluorescent resin.

The fluorescent additive may include a material that inherently has the fluorescence or that can have the fluorescence by, including but not limited to, an exposure process, a development process, and/or a bake process. That is, for example, the fluorescent additive may include a dye (e.g., a cyanine dye such as Cy5 or ALEXA Fluor 647 Dye®, a fluorescent dye produced by Molecular Probes, Inc.). In example embodiments, the photoresist layer 130 may include a plurality of fluorescent additives. The plurality of fluorescent additives may have fluorescent colors different from each other. That is, for example, the plurality of fluorescent additives may include a first fluorescent additive and a second fluorescent additive, which have fluorescent colors different from each other.

The fluorescent resin may include a resin that inherently has the fluorescence or that can have the fluorescence by, including but not limited to, the exposure process, the development process, and/or the bake process. The fluorescent resin may be manufactured by applying a nucleic acid stain technique. That is, for example, the fluorescent resin may include a polymer formed by chemically combining Hoechst 33258 (pentahydrate bis-benzimide) or Chromomycin A3 445 575 with a backbone chain.

Referring to FIG. 1 in conjunction with FIG. 2B, at S120, shown in FIG. 1, fluorescent photoresist patterns 132 may be formed on the anti-reflective layer (120). Forming the fluorescent photoresist patterns 132 may include performing a photolithography process on the photoresist layer 130. Performing the photolithography process may include but not limited to, exposing a portion of the photoresist layer 130 using a reticle exposing the portion of the photoresist layer 130, performing a post exposure bake (PEB) process, performing a development process to form the fluorescent photoresist patterns 132, and/or performing a hard bake process. The fluorescent photoresist patterns 132 may include fluorescence. This may be because the photoresist layer 130 includes at least one of the fluorescent additive or the fluorescent resin, as discussed above.

Referring to FIGS. 1, 2B, and 3, shapes of the fluorescent photoresist patterns 132 may be observed and/or inspected using a fluorescence microscope (S130). The fluorescence microscope may include but not limited to a super high-resolution microscope using reversible saturable optical fluorescence transitions (RESOLFT), or a stochastic functional technique. That is, for example, the microscope using the RESOLFT may include but not limited to, a stimulated emission depletion (STED) microscope, a ground state depletion (GSD) microscope, a saturated structured illumination microscope (SSIM), and/or a saturated pattern excitation microscope (SPEM). That is, for example, the microscope using the stochastic functional technique may be a spectral precision distance microscope (SPDM), a stochastic optical reconstruction microscope (STORM), a direct stochastic optical reconstruction microscope (dSTORM), a photo activated localization microscope (PALM), and/or a fluorescence photo-activation localization microscope (FPALM).

For operation S130, the observed and/or inspected shapes of the fluorescent photoresist patterns 132 may be compared with reference patterns (e.g., desired target photoresist patterns), thereby completing inspection and/or observation of the fluorescent photoresist patterns 132. Various methods may be used to determine the shapes of the fluorescent photoresist patterns 132. For example, as discussed above, a RESOLFT or stochastic functional technique may be used to determine the shapes of the fluorescent photoresist patterns 132. For example, an image of the fluorescent photoresist patterns 132 may be obtained using a sensor (e.g., camera) of the fluorescence microscope. In the captured images, pixels that correspond to the fluorescent photoresist patterns 132 may have a different intensity value than an intensity value of the pixels that do not correspond to the fluorescent photo resist patterns 132. As a result, the images of the fluorescent photoresist patterns 132 may be analyzed on a pixel-by-pixel basis to determine the shape of the fluorescent photoresist patterns 132. Also, the captured image of the fluorescent photoresist patterns 132 may be compared on a pixel-by-pixel basis with a reference image of the reference patterns to identify a degree of matching or mismatching. If the comparison result indicates that the degree of matching (or mismatching) between of the fluorescent photoresist patterns 132 and the reference patterns is an acceptable value, then the fluorescent photoresist patterns 132 may be used an etching mask in a subsequent process. Alternatively, if the comparison result indicates that the degree of matching (or mismatching) between of the fluorescent photoresist patterns 132 and the reference patterns is an unacceptable value, then the fluorescent photoresist patterns 132 may be reworked and re-inspected and/or re-observed.

Inspecting and/or observing the shapes of the fluorescent photoresist patterns 132, may include measuring one or more critical dimension (e.g., width and/or length) of the individual fluorescent photoresist patterns 132 or averages thereof and comparing the critical dimensions to a first threshold value (e.g., lower control limit) and a second threshold value (e.g., upper control limit) that is different than the first threshold value. If the comparison result indicates that the measured critical dimension (e.g., width and/or length) of the fluorescent photoresist pattern 132 is an acceptable value (e.g., the measured critical dimension is between the first and second threshold values), then the fluorescent photoresist patterns 132 may be used an etching mask in a subsequent process. Alternatively, if the comparison result indicates that the critical dimension is an unacceptable value (e.g., the measured critical dimension is outside of a range between the first and second threshold values), then the fluorescent photoresist patterns 132 may be reworked and re-inspected and/or re-observed. Reworking the fluorescent patterns 132 may include removing the fluorescent photoresist patterns 132, forming new fluorescent photoresist, and inspecting and/or observing the new fluorescent photoresist patterns 132.

In general, inspection and/or observing of a photoresist pattern may be performed using a scanning electron microscope (SEM). However, in the event that the inspection and/or observing of the photoresist pattern is performed using the SEM, a shape of the photoresist pattern may be deformed by an electron beam.

In the method for inspecting and/or observing the photoresist pattern according to example embodiments of inventive concepts, the inspection and/or observing of the photoresist pattern may be performed using the fluorescence microscope. When the photoresist pattern is inspected and/or observed using the fluorescence microscope, the photoresist pattern may be inspected and/or observed by applying relatively low energy (e.g., energy of visible light) to the photoresist pattern. Thus, it is possible to limit (and/or prevent) the shape of the photoresist pattern from being deformed in the process of inspecting and/or observing the photoresist pattern.

Additionally, the fluorescence microscope may be the super high-resolution microscope using the RESOLFT or the stochastic functional technique. Thus, a photoresist pattern having a very small critical dimension (CD) may be inspected and/or observed in example embodiments of inventive concepts. That is, for example, a photoresist pattern having a CD smaller than the Abbe diffraction limit (e.g., 200 nm (nanometer)) can be inspected and/or observed in example embodiments of inventive concepts.

Figure 4:
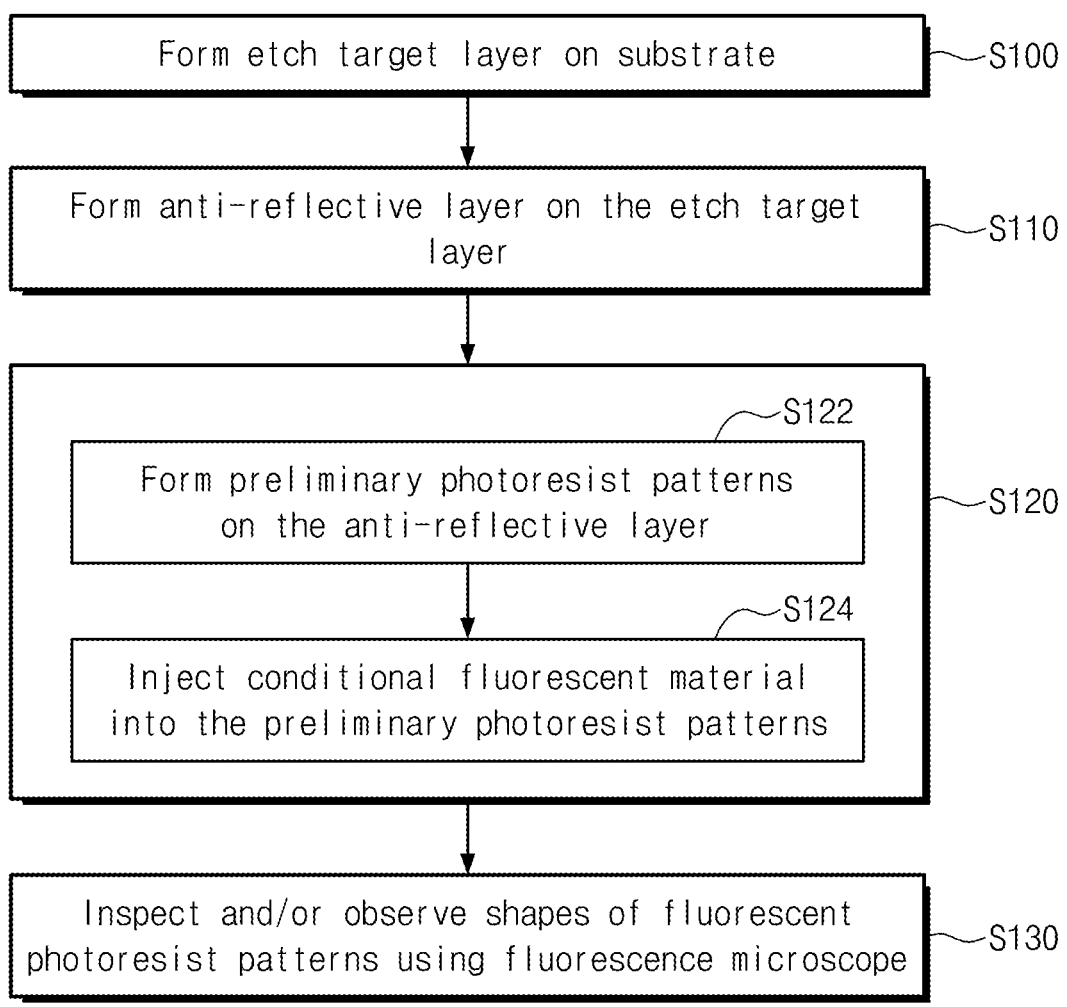
FIG. 4 is a flow chart illustrating a method for inspecting and/or observing a photoresist pattern, according to example embodiments of inventive concepts.
Figure 5A:
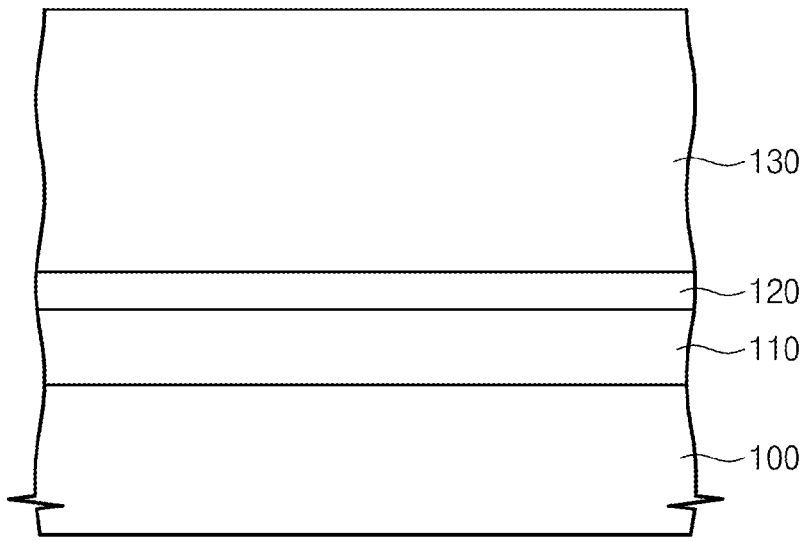
FIGS. 5A to 5C are cross-sectional views illustrating the method for inspecting and/or observing a photoresist pattern of FIG. 4.
Figure 5B:
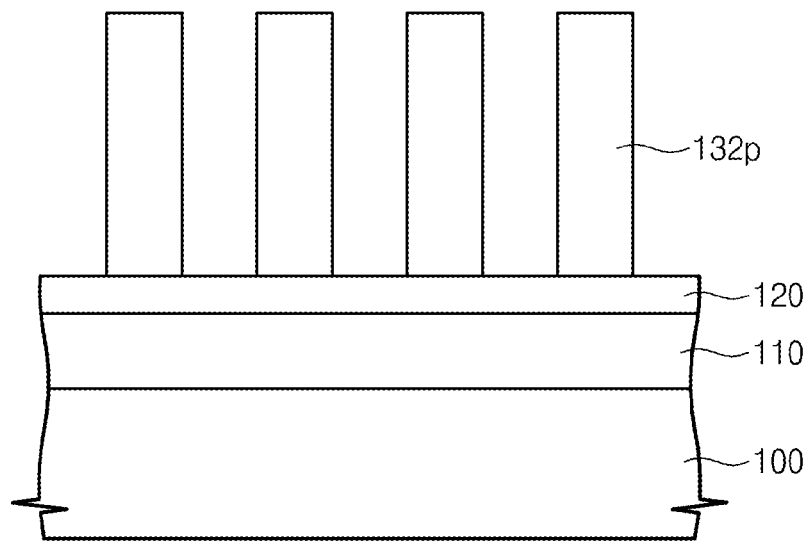
Figure 5C:
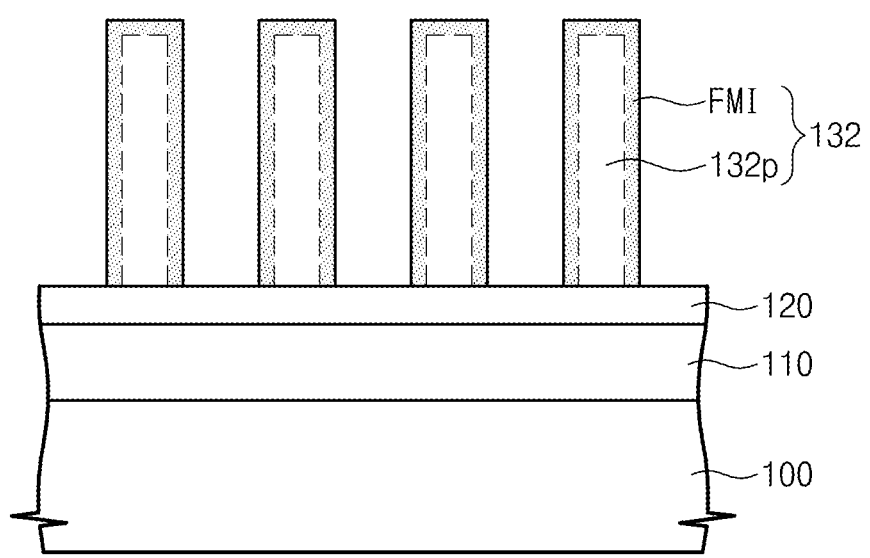

FIG. 4 is a flow chart illustrating a method for inspecting and/or observing a photoresist pattern, according to example embodiments of inventive concepts. FIGS. 5A to 5C are cross-sectional views illustrating the method for inspecting and/or observing a photoresist pattern of FIG. 4.

Hereinafter, a method for inspecting and/or observing a shape of a photoresist pattern according to example embodiments will be described with reference to FIGS. 3, 4, and 5A to 5C. The same elements as described with reference to FIGS. 1, 2A, 2B, and 3, will be indicated by the same reference numerals and/or the same reference designators. For the purpose of ease and convenience in explanation, the descriptions to the same elements and/or steps as in FIGS. 1, 2A, 2B, and 3 will be omitted and/or mentioned briefly.

Referring to FIGS. 4 and 5A, the etch target layer 110 and the anti-reflective layer 120 may be formed on the substrate 100 (S100 and S110). At S110, as shown in FIG. 5A, the anti-reflective layer 120 may be formed on the etch target layer 110. The processes of forming the etch target layer 110 and the anti-reflective layer 120 may be substantially the same and/or similar as described with reference to FIGS. 1 and 2A. Thus, the detailed descriptions thereto are omitted.

A photoresist layer 130 may be formed on the anti-reflective layer 120. The photoresist layer 130 may be formed by, for example, including but not limited to a spin coating process. The photoresist layer 130 may include at least a resin, a photosensitive material, and an additive. The photosensitive material may include a photo-acid generator (PGA).

In example embodiments, the photoresist layer 130 may not have fluorescence. For example, the photoresist layer 130 may not have both a fluorescent additive and a fluorescent resin. However, example embodiments of inventive concepts are not limited thereto. In example embodiments, the photoresist layer 130 may have the fluorescence. For example, the photoresist layer 130 may include at least one of the fluorescent additive or the fluorescent resin. The fluorescent additive and the fluorescent resin may be substantially the same as described with reference to FIGS. 1 and 2A. Hereinafter, the photoresist layer 130 not including the fluorescence will be described as an example for the purpose of ease and convenience in explanation.

Referring to FIGS. 4 and 5B, preliminary photoresist patterns 132p may be formed (S122) on the anti-reflective layer 120. Forming the preliminary photoresist patterns 132p may include performing a photolithography process on the photoresist layer 130. The preliminary photoresist patterns 132p formed by the photolithography process may include an acid generated by the photo-acid generator, and thus the preliminary photoresist patterns 132p may have acidity.

Referring to FIGS. 4 and 5C, a fluorescent material injection region FMI may be formed in each of the preliminary photoresist patterns 132p (S124). Forming the fluorescent material injection region FMI may be formed by injecting a conditional fluorescent material into each of the preliminary photoresist patterns 132p. The fluorescence of the conditional fluorescent material may be activated under an acid condition. That is, for example, the conditional fluorescent material may include CypHer5E (a pH sensitive dye made by GE Healthcare) or pHrodo® (a pH sensitive dye made by Thermo Fisher Scientific). The conditional fluorescent material injected in the fluorescent material injection region FMI may react with the acid included in the preliminary photoresist patterns 132p, and thus, the fluorescence of the conditional fluorescent material may be activated. In other words, the fluorescent material injection region FMI may have the fluorescence.

In example embodiments, the fluorescent material injection region FMI may be formed to have a specific depth from an exposed surface of the preliminary photoresist patterns 132p. In example embodiments, the conditional fluorescent material may be injected into each of the preliminary photoresist patterns 132p by a diffusion process, thereby forming the fluorescent material injection region FMI. That is, for example, the diffusion process may include a process of providing the substrate 100 having the preliminary photoresist patterns 132p into an atmosphere formed of the conditional fluorescent material in a gaseous state, and a process of thermally treating the substrate 100 having the preliminary photoresist patterns 132p. Thus, the conditional fluorescent material may be diffused into the preliminary photoresist patterns 132p to form the fluorescent material injection regions FMI in the preliminary photoresist patterns 132p, respectively. The preliminary photoresist patterns 132p in which the fluorescent material injection regions FMI are formed may be defined as fluorescent photoresist patterns 132 (S120).

The conditional fluorescent material may be injected into the anti-reflective layer 120 exposed between the preliminary photoresist patterns 132p by the diffusion process. However, the anti-reflective layer 120 may not have acidity, and thus fluorescence of the conditional fluorescent material injected in the anti-reflective layer 120 may not be activated. In other words, the anti-reflective layer 120 exposed between the preliminary photoresist patterns 132p may include the conditional fluorescent material but may not have the fluorescence.

Referring to FIGS. 3, 4, and 5C, shapes of the fluorescent photoresist patterns 132 may be observed and/or inspected using a fluorescence microscope (S130). Observing and/or inspecting the fluorescent photoresist patterns 132 using the fluorescence microscope may be substantially the same as described with reference to FIGS. 1, 2B, and 3.

Figure 6:
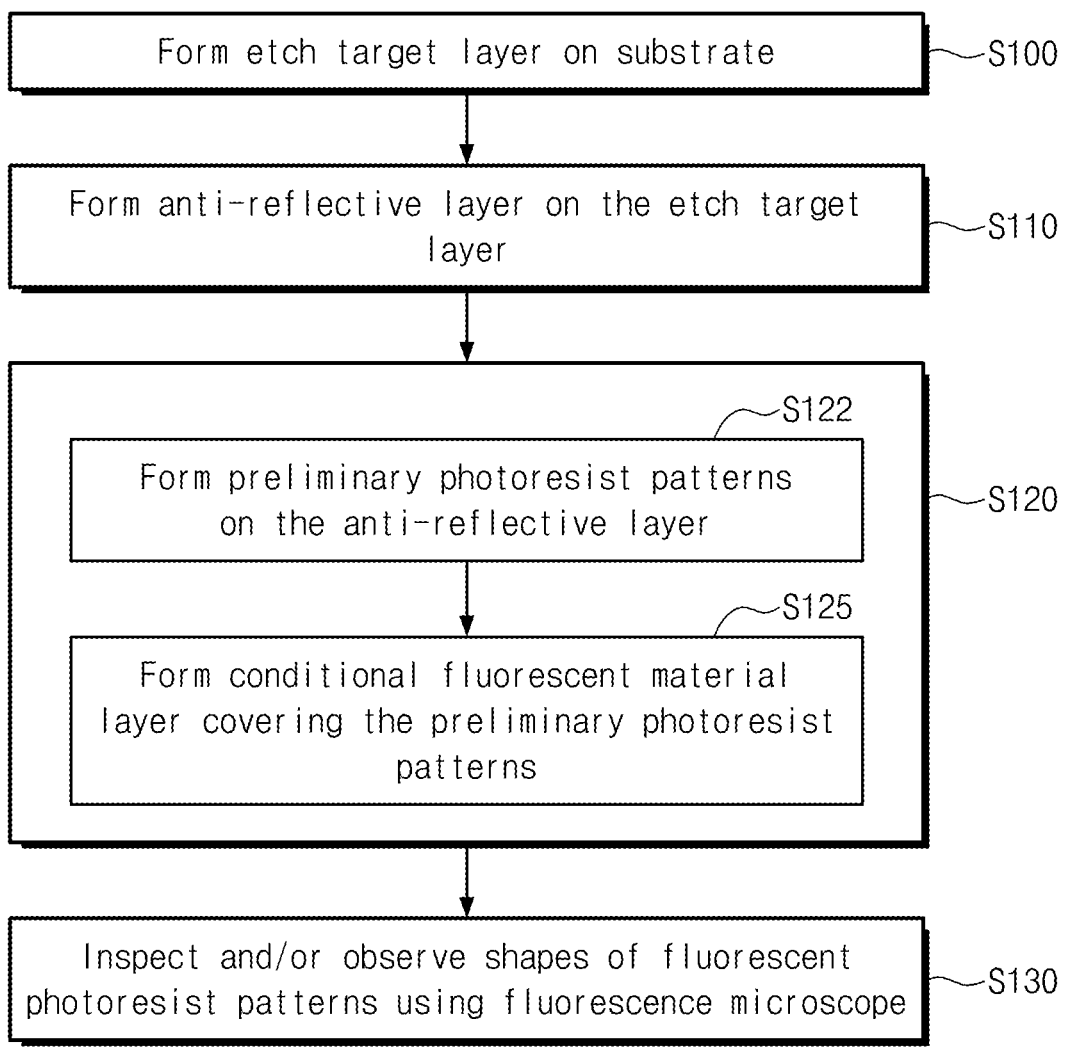
FIG. 6 is a flow chart illustrating a method for inspecting and/or observing a photoresist pattern, according to example embodiments of inventive concepts.
Figure 7:
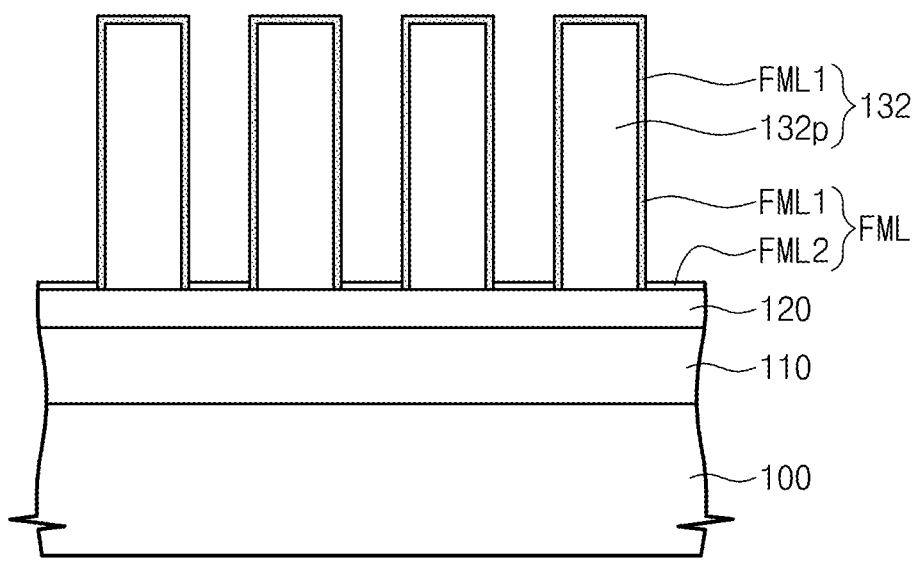
FIG. 7 is a cross-sectional view illustrating the method for inspecting and/or observing a photoresist pattern of FIG. 6.
Figure 8:
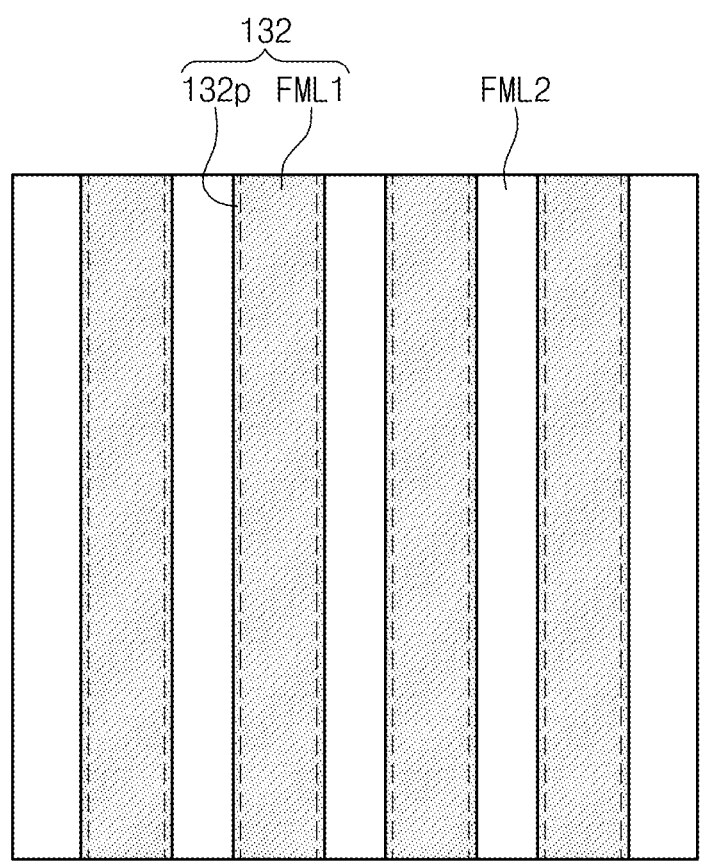
FIG. 8 schematically illustrates a planar image of a structure of FIG. 7 obtained using a fluorescence microscope.

FIG. 6 is a flow chart illustrating a method for inspecting and/or observing a photoresist pattern, according to some example embodiments of inventive concepts. FIG. 7 is a cross-sectional view illustrating the method for inspecting and/or observing a photoresist pattern of FIG. 6. FIG. 8 schematically illustrates a planar image of a structure of FIG. 7 obtained using a fluorescence microscope.

Hereinafter, a method for inspecting and/or observing a shape of a photoresist pattern will be described with reference to FIGS. 6, 7, and 8. The same elements as described in the embodiment of FIGS. 3, 4, and 5A to 5C will be indicated by the same reference numerals or the same reference designators. For the purpose of ease and convenience in explanation, the descriptions to the same elements and/or steps as in example embodiment of FIGS. 3, 4, 5A to 5C will be omitted and/or briefly mentioned.

Referring to FIGS. 6 and 7, the etch target layer 110 may be formed on the substrate 100 the anti-reflective layer 120, and the preliminary photoresist patterns 132p may be sequentially formed on the substrate 100 (S100, S110, and S122). The processes of forming the etch target layer 110, the anti-reflective layer 120, and the preliminary photoresist patterns 132p may be substantially the same as described with reference to FIGS. 4, 5A, and 5B, and thus the detailed descriptions thereto is omitted.

A conditional fluorescent material layer FML may be formed on the substrate 100, such that the conditional fluorescent material layer FML may cover the preliminary photoresist patterns 132p (S125). The conditional fluorescent material layer FML may include a material of which fluorescence is activated under an acid condition. That is, for example, the conditional fluorescent material layer FML may include CypHer5E (a pH sensitive dye made by GE Healthcare) or pHrodo® (a pH sensitive dye made by Thermo Fisher Scientific). For example, the conditional fluorescent material layer FML may be formed using a CVD method, a PVD method, or an ALD method.

The conditional fluorescent material layer FML may include first portions FML1 covering the preliminary photoresist patterns 132p, and second portions FML2 covering portions of the anti-reflective layer 120, respectively. The second portions FML2 may be exposed between the preliminary photoresist patterns 132p. The first portions FML1 may be in contact with the preliminary photoresist patterns 132p. Accordingly, the first portions FML1 may react with the acid included in the preliminary photoresist patterns 132p, and thus the fluorescence of the first portions FML1 may be activated. In other words, the first portions FML1 may have the fluorescence. The preliminary photoresist patterns 132p may be formed on the anti-reflective layer 120 (S122). As shown in FIG. 7, the photoresist patterns 132p may be covered with the first portions FML1. The photoresist patterns 132p and the first portions FML1, in combination, may define as the fluorescent photoresist patterns 132 (S120). The second portions FML2 may be in contact with the portions of the anti-reflective layer 120 exposed between the preliminary photoresist patterns 132*p*, and may be spaced apart from the preliminary photoresist patterns 132*p*. As described above, the anti-reflective layer 120 may not have acidity, and thus, fluorescence of the second portions FML2 may not be activated. In other words, the second portions FML2 may not have the fluorescence.

Referring to FIGS. 6, 7, and 8, shapes of the fluorescent photoresist patterns 132 may be observed and/or inspected using a fluorescence microscope (S130). Observing and/or inspecting the fluorescent photoresist patterns 132 using the fluorescence microscope may be substantially the same as described with reference to FIGS. 1, 2B, and 3.

Figure 9:
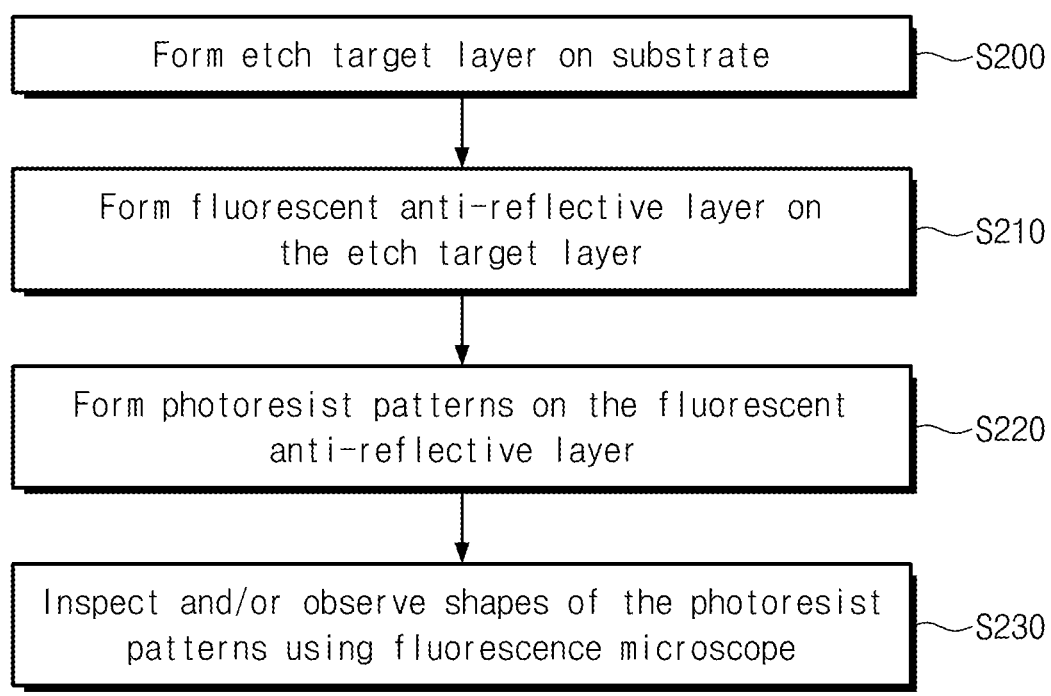
FIG. 9 is a flow chart illustrating a method for inspecting and/or observing a photoresist pattern, according to example embodiments of inventive concepts.
Figure 10A:
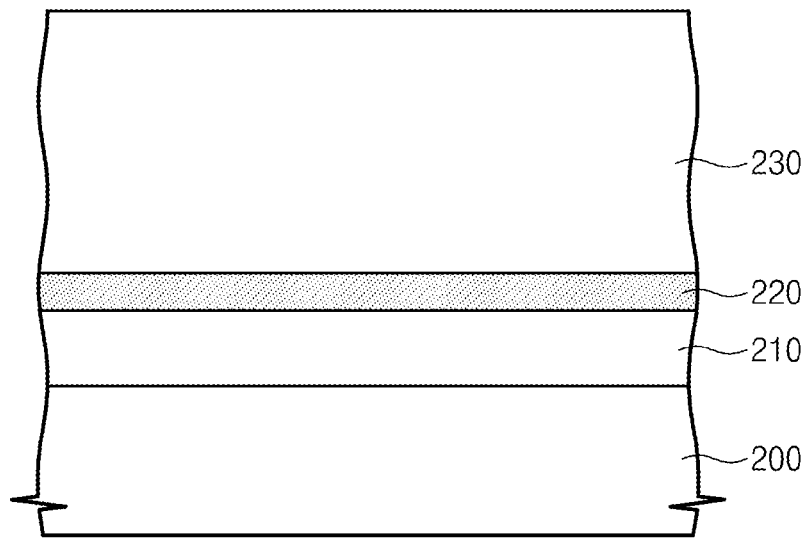
FIGS. 10A and 10B are cross-sectional views illustrating the method for inspecting and/or observing a photoresist pattern of FIG. 9.
Figure 10B:
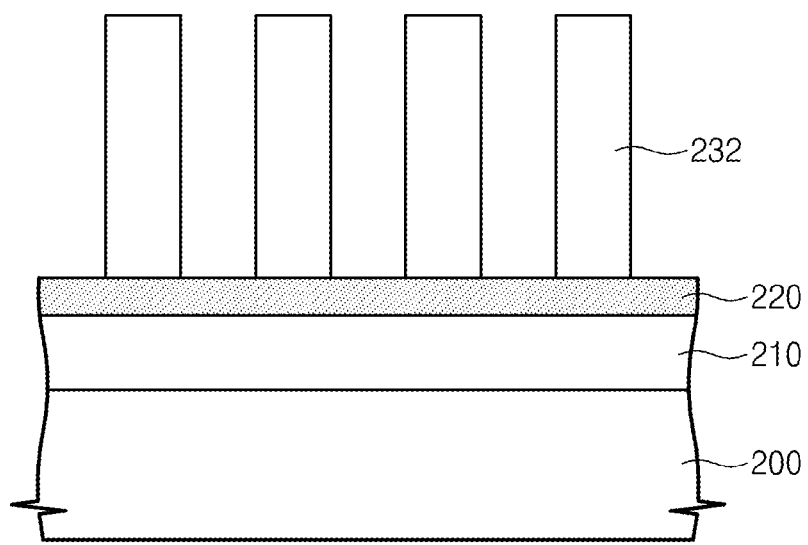
Figure 11:
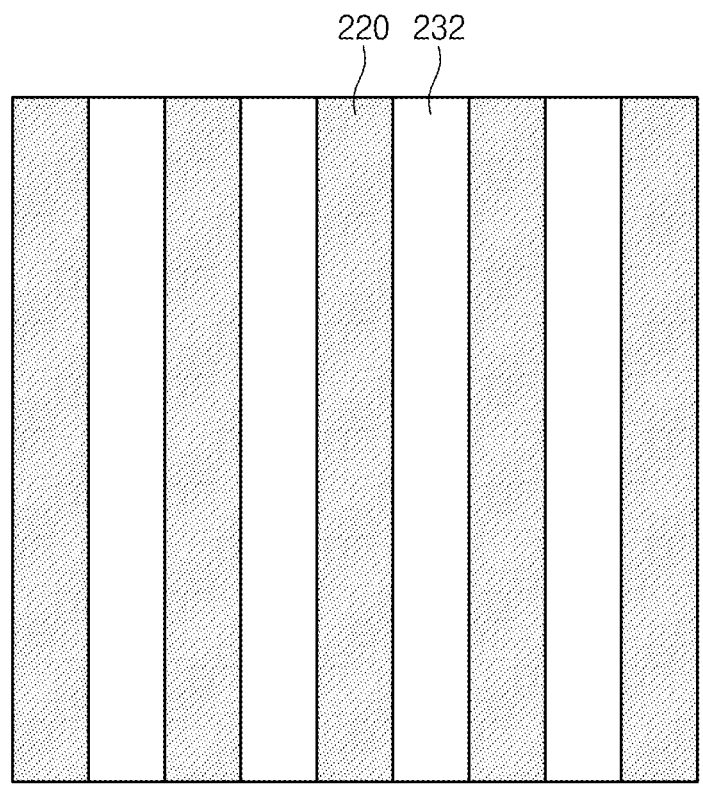
FIGS. 11 and 12 schematically illustrate planar images of a structure of FIG. 10B obtained using a fluorescence microscope, respectively.
Figure 12:
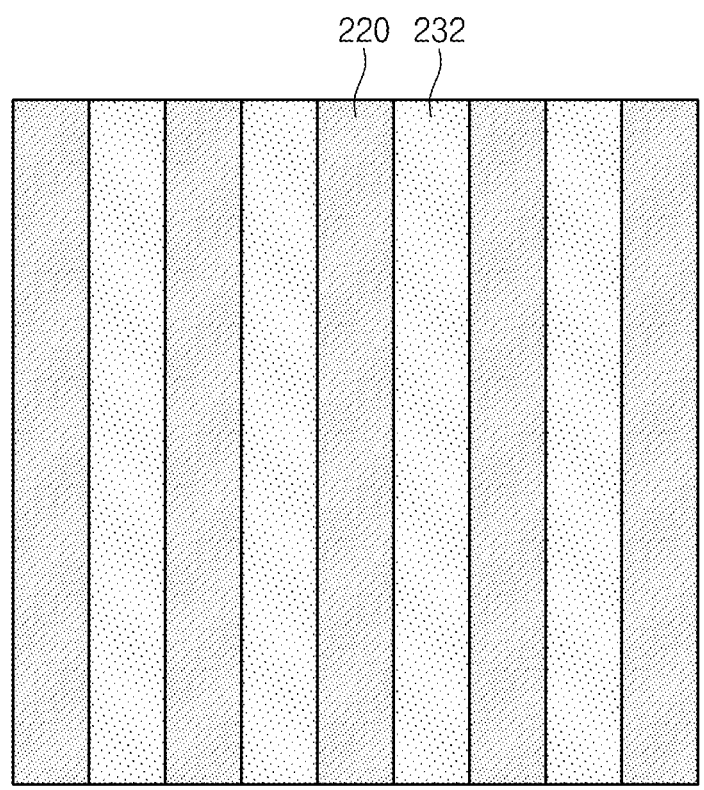

FIG. 9 is a flow chart illustrating a method for observing and/or inspecting a photoresist pattern, according to some example embodiments of inventive concepts. FIGS. 10A and 10B are cross-sectional views illustrating the method for observing and/or inspecting a photoresist pattern of FIG. 9. FIGS. 11 and 12 schematically illustrate planar images of a structure of FIG. 10B obtained using a fluorescence microscope.

Hereinafter, a method for observing and/or inspecting a shape of a photoresist pattern will be described with reference to FIGS. 9, 10A, 10B, 11, and 12. The descriptions to the same technical features as in FIGS. 1, 2A, 2B, and 3 will be omitted or briefly mentioned for the purposes of ease and convenience.

Referring to FIGS. 9 and 10A, an etch target layer 210 may be formed on a substrate 200 (S200). The substrate 200 may be, including but not limited to, a semiconductor substrate, a glass substrate, and/or a polymer substrate. In example embodiments, when the substrate 200 is a semiconductor substrate, the substrate 200 may include at least one of, including but not limited to, crystalline silicon, amorphous silicon, silicon doped with dopants, or silicon-germanium.

The etch target layer 210 may include at least a semiconductor material, a conductive material, and/or an insulating material. In example embodiments where the etch target layer 210 includes the semiconductor material, the etch target layer 210 may be a portion of the semiconductor substrate 200, an epitaxial layer formed of a semiconductor material, and/or a semiconductor layer deposited on the substrate 200. In example embodiments where the etch target layer 210 includes the conductive material, the etch target layer 210 may include doped poly-silicon, a metal, a metal silicide, a metal nitride, or any combination thereof.

In example embodiments, when the etch target layer 210 includes the insulating material, the etch target layer 210 may include at least silicon oxide, silicon nitride, or silicon oxynitride. The etch target layer 210 may be a single layer and/or a multi-layer including a plurality of stacked layers. In example embodiments, the etch target layer 210 may include a plurality of stacked insulating layers and a conductive or semiconductor layer disposed between the stacked insulating layers. The etch target layer 210 may be formed using, for example, a CVD method, a PVD method, and/or an ALD method.

A fluorescent anti-reflective layer 220 may be formed on the etch target layer 210 (S210). The fluorescent anti-reflective layer 220 may limit (and/or prevent) uniformity of critical dimensions of photoresist patterns 232 of FIG. 10B to be described later from being deteriorated by reflected light in a subsequent photolithography process. The fluorescent anti-reflective layer 220 may be formed by, for example, a spin coating process.

The fluorescent anti-reflective layer 220 may include a fluorescent additive. The fluorescent additive may include a material that inherently has the fluorescence or that can have the fluorescence by an exposure process, a development process, and/or a bake process. That is, for example, the fluorescent additive may include Cy5 or Alexa647. In example embodiments, the fluorescent anti-reflective layer 220 may include a plurality of fluorescent additives. In example embodiments, the plurality of fluorescent additives may have fluorescent colors different from each other. For example, the plurality of fluorescent additives may include a first fluorescent additive and a second fluorescent additive, which have fluorescent colors different from each other.

A photoresist layer 230 may be formed on the fluorescent anti-reflective layer 220. In example embodiments, the photoresist layer 230 may not have fluorescence. In other words, the photoresist layer 230 may not have both a fluorescent additive and a fluorescent resin. Alternatively, in example embodiments, the photoresist layer 230 may have fluorescence. In example embodiments, a fluorescent color of the photoresist layer 230 may be different from that of the fluorescent anti-reflective layer 220. In example embodiments, the photoresist layer 230 may include at least one of a fluorescent additive or a fluorescent resin. The fluorescent additive or the fluorescent resin may be the same as described with reference to FIGS. 1 and 2A. Hereinafter, the photoresist layer 230 not having the fluorescence will be described as an example for the purposes of ease and convenience.

Referring to FIGS. 9 and 10B, photoresist patterns 232 may be formed (S220). Forming the photoresist patterns 232 may include performing a photolithography process on the photoresist layer 230. A portion of the fluorescent anti-reflective layer 220 may be exposed by the photoresist patterns 232.

Referring to FIGS. 9, 10B, 11, and 12, the photoresist patterns 232 may be observed and/or inspected using a fluorescence microscope (S230). The fluorescence microscope may be a super high-resolution microscope using reversible saturable optical fluorescence transitions (RESOLFT) or a stochastic functional technique. That is, for example, the microscope using the RESOLFT may be a stimulated emission depletion (STED) microscope, a ground state depletion (GSD) microscope, a saturated structured illumination microscope (SSIM), and/or a saturated pattern excitation microscope (SPEM). For example, the microscope using the stochastic functional technique may be a spectral precision distance microscope (SPDM), a stochastic optical reconstruction microscope (STORM), a direct stochastic optical reconstruction microscope (dSTORM), a photo activated localization microscope (PALM), and/or a fluorescence photo-activation localization microscope (FPALM).

In example embodiments, as illustrated in FIG. 11, light generated from the fluorescent anti-reflective layer 220 may not pass through the photoresist patterns 232. In this case, a planar image of portions, exposed by the photoresist patterns 232, of the fluorescent anti-reflective layer 220 may be observed and/or inspected through the fluorescence microscope, and thus a planar image of the photoresist patterns 232 may be obtained using the fluorescence microscope. For example, the contrast of the planar image of the exposed portions of the fluorescent anti-reflective layer 220 may be reversed to obtain the planar image of the photoresist patterns 232.

In example embodiments, as illustrated in FIG. 12, light generated from the fluorescent anti-reflective layer 220 may pass through the photoresist patterns 232. The light generated from the fluorescent anti-reflective layer 220 may be refracted while passing through the photoresist patterns 232, and thus the light transmitted from the photoresist patterns 232 may be distorted and then observed and/or inspected. In other words, the light passing through the photoresist patterns 232 and the light not passing through the photoresist patterns 232 may be distinguished from each other by the fluorescence microscope. Thus, the planar image of the photoresist patterns 232 may be obtained using the fluorescence microscope.

The observed and/or inspected shapes of the photoresist patterns 232 may be compared with reference patterns (e.g., desired target photoresist patterns), thereby completing inspection and/or observation of the photoresist patterns 232. The inspection and/or observation of the photoresist patterns 232 in operation S230 may be the same as or similar to the inspection and/or observation of the photoresist patterns 132 in operation S130, as discussed above. If the inspection and/or observation of the photoresist patterns 232 indicates that the photoresist patterns 232 are acceptable, then the photoresist patterns 232 may be used as an etching mask in a subsequent process. Alternately, if the inspection and/or observation of the photoresist patterns 232 indicates that the photoresist patterns 232 are not acceptable (e.g., critical dimension is outside of an acceptable range) then the photoresist patterns 232 may be reworked and re-inspected and/or re-observed.

In the method for inspecting and/or observing the photoresist pattern according to some example embodiments of inventive concepts, the inspection and/or observation of the photoresist pattern may be performed using the fluorescence microscope. When the photoresist patterns are inspected and/or observed using the fluorescence microscope, the photoresist patterns may be inspected and/or observed by applying relatively low energy (e.g., energy of visible light) to the photoresist patterns. Thus, it is possible to inhibit the shape of the photoresist patterns from being deformed in the process of inspecting and/or observing the photoresist patterns.

In addition, the fluorescence microscope may be the super high-resolution microscope using the RESOLFT or the stochastic functional technique. Thus, a photoresist pattern having a very small critical dimension (CD) may be inspected and/or observed in example embodiments of inventive concepts. For example, a photoresist pattern having a CD smaller than the Abbe diffraction limit (e.g., 200 nm) can be inspected and/or observed in example embodiments of inventive concepts.

While inventive concepts have been described with reference to example embodiments, it will be apparent to those skilled in the art that various changes and modifications may be made without departing from the spirits and scopes of the inventive concepts. Descriptions of features or aspects within each device or method according to example embodiments should typically be considered as available for other similar features or aspects in other devices or methods according to example embodiments. Therefore, it should be understood that the above example embodiments are not limiting, but illustrative. Thus, the scopes of inventive concepts are to be determined by the broadest permissible interpretation of the following claims and their equivalents, and shall not be restricted or limited by the foregoing description.

What is claimed is:

1. A method for inspecting a photoresist pattern, the method comprising:
   forming an anti-reflective layer on a substrate;
   forming fluorescent photoresist patterns on the anti-reflective layer, the fluorescent photoresist patterns having fluorescence; and
   inspecting a shape of the fluorescent photoresist patterns using a fluorescence microscope,
   wherein the forming the fluorescent photoresist patterns includes,
      forming a photoresist layer on the anti-reflective layer,
      performing a photolithography process on the photoresist layer to form preliminary photoresist patterns,
      injecting a conditional fluorescent material into the preliminary photoresist patterns, the conditional fluorescent material having a property of showing fluorescence under an acid condition, and
   wherein a location of the fluorescent photoresist patterns corresponds to a location of the preliminary photoresist patterns.

2. The method of claim 1, wherein the injecting the conditional fluorescent material includes reacting the condition fluorescent material with an acid included in the preliminary photoresist patterns to show the fluorescence.

3. The method of claim 1, wherein the fluorescence microscope is a microscope configured to use at least one of reversible saturable optical fluorescence transitions (RESOLFT) and a stochastic functional technique.

4. A method for inspecting a photoresist pattern, the method comprising:
   forming an anti-reflective layer on a substrate;
   forming a fluorescent photoresist pattern on the anti-reflective layer, the fluorescent photoresist pattern having fluorescence,
   the forming the fluorescent photoresist pattern including forming a photoresist layer on the anti-reflective layer, performing a photolithography process on the photoresist layer to form a preliminary photoresist pattern, and injecting a conditional fluorescent material into the preliminary photoresist pattern, wherein
      the conditional fluorescent material has a property of showing fluorescence under an acid condition,
      a location of the fluorescent photoresist pattern corresponds to a location of the preliminary photoresist pattern,
      the injecting the conditional fluorescent material includes injecting the conditional fluorescent material into the anti-reflective layer exposed by the preliminary photoresist pattern, and
      the conditional fluorescent material injected in the anti-reflective layer does not show the fluorescence; and
   inspecting a shape of the fluorescent photoresist pattern using a fluorescence microscope.

* * * * *